United States Patent [19]

Kane

[11] Patent Number: 5,182,399
[45] Date of Patent: Jan. 26, 1993

[54] PROCESS FOR PREPARING PIPERIDINYL BENZIMIDAZOLES

[75] Inventor: John M. Kane, Cincinnati, Ohio
[73] Assignee: Merrell Dow Pharmaceuticals Inc., Cincinnati, Ohio
[21] Appl. No.: 732,994
[22] Filed: Jul. 18, 1991

Related U.S. Application Data

[60] Continuation of Ser. No. 452,920, Dec. 18, 1989, abandoned, which is a division of Ser. No. 256,959, Oct. 13, 1988, Pat. No. 4,908,372.

[51] Int. Cl.$^5$ ............................................. C07D 401/06
[52] U.S. Cl. ............................................................ 546/199
[58] Field of Search ........................................ 546/199

[56] References Cited

PUBLICATIONS

Ohta et al., *Chem. Pharm. Bull.* (Japan) 34(12), 4916 (1986).
A. Katritzky et al., *Comprehensive Heterocyclic Chemistry*, vol. 5, Part 4A, Pergamon Press, Oxford, 1984, p. 401.

*Primary Examiner*—Joseph Paul Brust
*Assistant Examiner*—Jacqueline Haley
*Attorney, Agent, or Firm*—Neal O. Willmann

[57] ABSTRACT

The present invention is directed to a new class of piperidinyl benzimidazole antihistamines which can be described by the following formula:

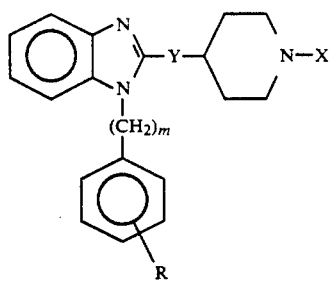

FORMULA I wherein Y is represented by CO or CHOH; m is an integer from 1 to 2; R is represented by $C_{1-4}$ alkyl, $C_{1-4}$ alkoxy, halogen, hydroxy and hydrogen; X is represented by hydrogen, $COOR_2$, in which $R_2$ is represented by a $C_{1-4}$ alkyl, or an alkylene phenyl radical of the formula:

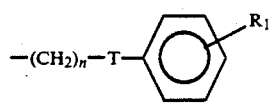

FORMULA II wherein T is represented by CHOH, CO, O, or a direct bond; $R_1$ is represented by $C_{1-4}$ alkyl, $C_{1-4}$ alkoxy, halogen, hydroxy, 2,2-dimethyl ethanoic acid and hydrogen; n is an integer from 1 to 5; and the pharmaceutically acceptable acid addition salts thereof.

7 Claims, No Drawings

PROCESS FOR PREPARING PIPERIDINYL BENZIMIDAZOLES

This is a continuation of application Ser. No. 07/452,920, filed Dec. 18, 1989, now abandoned which is a divisional of application Ser. No. 07/256,959, filed Oct. 13, 1988, now U.S. Pat. No. 4,908,372.

The present invention is directed to a class of piperidinyl benzimidazole antihistamines. An additional aspect of the invention is directed to a method for treating allergic diseases. Another aspect of the present invention is directed to intermediates useful in the synthesis of said piperidinyl benzimidazole antihistamines. A further aspect of the present invention is directed to a process for the production of the piperidinyl benzimidazole antihistamines A final aspect is directed to a pharmaceutical composition containing said piperidinyl benzimidazole antihistamines.

In accordance with the present invention, a new class of piperidinyl benzimidazole antihistamines has been discovered which can be described by the following formula:

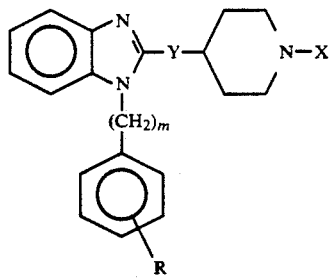

FORMULA I wherein Y is represented by CO or CHOH; m is an integer from 1 to 2; R is represented by $C_{1-4}$ alkyl, $C_{1-4}$ alkoxy, halogen, hydroxy and hydrogen; X is represented by hydrogen, $COOR_2$, in which $R_2$ is represented by a $C_{1-4}$ alkyl, or an alkylene phenyl radical of the formula:

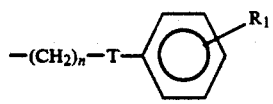

FORMULA II wherein T is represented by CHOH, CO, O, or a direct bond; $R_1$ is represented by $C_{1-4}$ alkyl, $C_{1-4}$ alkoxy, halogen, hydroxy, 2,2-dimethyl ethanoic acid and hydrogen; n is an integer from 1 to 5; and the pharmaceutically acceptable acid addition salts thereof.

The compounds of Formula I are histamine ($H_1$) antagonists. Some of the compounds encompassed by Formula I are also peripheral serotonin $5HT_2$ antagonists. The compounds of Formula I are effective in the treatment of allergic diseases.

As used in this application
a) the term halogen refers to a fluorine, chlorine, or bromine atom;
b) the term $C_{1-4}$ alkyl refers to a branched or straight chained alkyl group containing from 1–4 carbon atoms, such as methyl, ethyl, n-propyl, isopropyl, n-butyl, isobutyl and t-butyl;
c) the term $C_{1-4}$ alkoxy refers to a straight or branched alkoxy group containing from 1–4 carbon atoms, such as methoxy, ethoxy, n-propoxy, isopropoxy, n-butoxy, isobutoxy and t-butoxy;
d) the term CO refers to a carbonyl group having the following structure:

e) the term CHOH refers to a hydroxymethylene group;
f) the term hydroxy refers to the following substituent, —OH;
g) the term —$C_6H_5$ refers to a phenyl radical;
h) the term 2,2-dimethyl ethanoic acid refers to the following substituent.

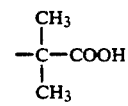

i) the term alkyl haloformate refers to the following compound in which A is a halogen atom and $R_2$ is a $C_{1-4}$ alkyl:

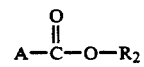

j) the term ketal refers to the following substituent:

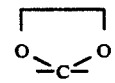

The expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methane sulfonic acid and 2-hydroxyethane sulfonic acid. Either the mono- or di-acid salts can be formed, and such salts can exist in either a hydrated or substantially anhydrous form. In general, the acid addition salts of these compounds show increased solubility in water and various hydrophilic organic solvents and which in comparison to their free base forms, generally demonstrate higher melting points.

Some of the compounds of Formula I contain asymmetric centers. Any reference in this application to one of the compounds represented by Formula I is meant to encompass either a specific optical isomer or a mixture of enantiomers or diasteriomers. The specific optical isomers can be separated and recovered by techniques known in the art such as chromatography on chiral stationary phases or resolution via chiral salt formation and subsequent separation by selective crystallization.

In the compounds of Formula I wherein R is other than hydrogen, there can be up to 3 such substituents occurring on the indicated phenyl ring These substituents can be the same or can differ. These substituents can be located at any of the ortho, meta, or para positions. In those compounds in which $R_1$ is other than hydrogen or a t-butyl group, there can be up to 3 substituents occurring on the indicated phenyl ring These substituents can be the same or differ and can be located at any of the ortho, meta, or para positions. If $R_1$ is a t-butyl group or a derivative thereof, then there should only be one such substituent appearing on the indicated phenyl ring and it should be located at the para position.

Preferred compounds include those in which Y is represented by CO, m is 1 and R is a para-halogen, more preferably fluorine. In those compounds in which Y is represented by an alkylene phenyl derivative, it is preferred that T be represented by a direct bond, n is 1 and that $R_1$ is a para-alkoxy group.

Illustrative examples of compounds encompassed by Formula I include:

a) 1-[(4-fluorophenyl)methyl]-1H-benzimidazol-2-yl][1-[2(4-methoxyphenyl)ethyl]-4-piperidinyl]methanone;

b) 1-[(4-fluorophenyl)methyl]-α-[1-[2-(4-methoxyphenyl) ethyl]-4-piperidinyl]-1H-benzimidazole-2-methanol;

c) α-[1-[4-[4-(1,1-dimethylethyl)phenyl]-4-hydroxybutyl]-4-piperidinyl]-1-[(4-fluorophenyl)methyl]-1H-benzimidazole-2-methanol;

d) 1-[4-(1,1-dimethylethyl) phenyl]-4-[4-[[1-[(4-fluorophenyl)methyl]-1H-benzimidazol-2-yl]carbonyl]-1piperidinyl]-1-butanone, and;

e) [1-[(4-fluorophenyl)methyl]-1H-benzimidazol-2-yl]-4-piperidinylmethanone.

The compounds of Formula I wherein Y is represented by a carbonyl group (CO) and X is represented by either $COOR_2$ or an alkylene phenyl derivative as described by Formula II in which T represented by either O or a direct bond, can be produced by conducting an acylation reaction between a piperidinyl derivative as described by Formula III and a benzimidazole derivative as described by Formula IV:

FORMULA III

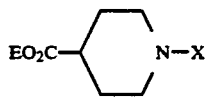

FORMULA IV

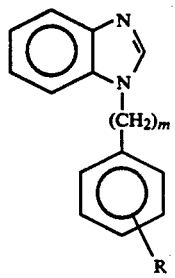

In Formula III, E is represented a $C_{1-4}$ alkyl and X is either $COOR_2$ or an alkylene derivative as described by Formula II in which T is either O or a direct bond. In Formula IV, R and m are as defined in Formula I.

As is apparent to those skilled in the art, it is preferred that the non-reacting substituents appearing in the piperidinyl derivative of Formula III and the benzimidazole derivative of Formula IV correspond to those appearing in the final product.

For example if the desired piperidinyl benzimidazole is [1-[(4-fluorophenyl)methyl]-1H-benzimidazol-2-yl][1-[2-(4-methoxyphenyl)ethyl]-4-piperidinyl]methanone, then 1-[(4-fluorophenyl)methyl]-1H-benzimidazole should be reacted with 1-[2-(4-methoxyphenyl)ethyl]-4-piperidine carboxylic acid, methyl ester.

The acylation reactions between the benzimidazole derivative of Formula IV and the piperidinyl derivatives of Formula III are conducted in the following manner.

Typically, a solution of the benzimidazole derivative of Formula IV will be contacted with an organolithium compound such as n-butyl lithium for a period of time ranging from about 5 minutes to about 30 minutes and more preferably about 15 minutes; at temperature range of from about −90° C. to about −50° C. and more preferably about −78° C. The organolithium compound will be present in the quantity of from about 1.0 to about 1.1 equivalents for every mole of benzimidazole derivative utilized, and more preferably will be present in an approximately equimolar quantity with the benzimidazole derivative. The reaction is typically conducted in an organic solvent such as, tetrahydrofuran.

The piperidinyl derivative of Formula III is then added to the reaction medium and the reaction medium is warmed from about −78° C. to about 0° C. The piperidinyl derivative and the benzimidazole derivative are preferably present in the reaction zone in an approximately equimolar quantity. A slight excess of either reactant is not deleterious to the reaction The reaction is allowed to proceed for a period of time ranging from about 20 minutes to about 5 hours, and more preferably about 30 minutes. The reaction is then quenched with a proton source such as, for example, saturated aqueous ammonium chloride or methanol.

The piperidinyl benzimidazole derivatives of Formula I can be recovered from the reaction zone according to techniques known in the art such as extraction with ethyl acetate after the addition of water The desired piperidinyl benzimidazole will be located in the organic phase. The organic phase is typically dried and concentrated prior to further purification utilizing conventional techniques.

The piperidinyl benzimidazole can be purified according to techniques known in the art. For example, one suitable technique is to subject the concentrate obtained above to flash chromatography utilizing an organic solvent such as ethyl acetate as the eluting agent The eluent can be evaporated and the resulting product can be recrystallized from a suitable solvent such as, for example, cyclohexane. Other suitable solvent systems will be readily apparent to those skilled in the art.

Those piperidinyl derivatives of Formula III in which X is represented by an alkylene phenyl derivative in which T is either O or a direct bond are produced in the following manner. A piperidinyl derivative as described by Formula V is N-alkylated with an alkylene phenyl derivative as described by Formula VI:

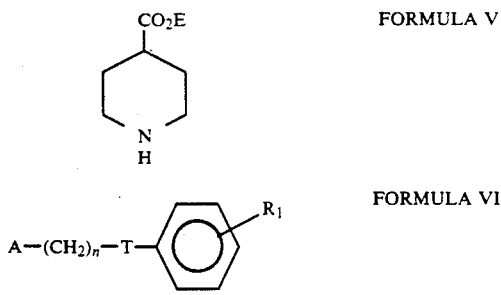

FORMULA V

FORMULA VI in which E is represented by a $C_{1-4}$ alkyl, A is represented by a halogen atom, T is O or a direct bond and $R_1$ and n are as defined in Formula II.

As is apparent to those skilled in the art, it is preferred that the non-reacting substituents appearing in the piperidinyl derivative of Formula V and the alkylene phenyl derivative of Formula VI correspond to those appearing in the final product For example if the desired piperidinyl intermediate of Formula III is 1-[2-(4-methoxyphenyl) ethyl]-4-piperidine carboxylic acid, methyl ester, then the proper reactants are isonipecotic acid methyl ester and 1-(2-haloethyl)-4-methoxybenzene.

The N-alkylation reaction can be accomplished according to techniques known in the art. This N-alkylation reaction is typically conducted in the presence of a base such as $K_2CO_3$, $Na_2CO_3$, $NaHCO_3$, or $KHCO_3$. Typically the base will be present in the reaction zone in a quantity of from about 1 equivalents to about 3 equivalents for every mole of the piperidinyl derivative which is utilized.

It is preferred that the piperidinyl derivative of Formula V and the alkylene phenyl derivative of Formula VI be present in the reaction zone in approximately equimolar quantities. A moderate excess of either reactant is not deleterious to the reaction however. It is also preferred that the reaction be conducted at elevated temperatures. Typically the reactants are stirred together at a temperature range of from about 50° C. to about 100° C. for a period of time ranging from about 30 minutes to about 48 hours. The reaction is also typically conducted in an organic solvent such as dimethylformamide, acetonitrile, dimethyl sulfoxide, benzene and toluene.

The piperidinyl derivative of Formula III can be recovered and purified according to techniques known in the art. For example after the addition of water, the piperidinyl derivative can be recovered by extraction with an organic solvent. The desired piperidinyl compound will be located in the organic phase. The piperidinyl compound can be purified by flash chromatography utilizing an organic solvent such as ethyl acetate or acetone as the eluting agent followed by recrystallization from a solvent system such as, for example, cyclohexane. Other suitable purification techniques will be readily apparent to those skilled in the art.

Some of the piperidinyl derivatives of Formula III in which X is represented by $COOR_2$ are known in the art. These compounds, as well as those not known in the art can be prepared using methods well known in the art.

For example, the piperidinyl derivative of Formula V can be reacted with an alkyl haloformate in the presence of a base such as $K_2CO_3$, $KHCO_3$, $Na_2CO_3$, $NaHCO_3$, or triethylamine. Typically the reactants will be stirred together for a period of time ranging from about 30 minutes to about 48 hours, at a temperature range of from about 0° C. to about 100° C. It is preferred that the non-reacting substituents appearing in the alkyl haloformate correspond to those appearing in the product. The piperidinyl derivative can be recovered from the reaction zone by treatment with water and extraction with an organic solvent as is known in the art. It can be purified by techniques known in the art such as recrystallization from an appropriate solvent system or distillation.

The benzimidazole derivative of Formula IV can be prepared according to techniques known in the art. The starting materials are a benzimidazole as described by Formula VII and an alkylene phenyl derivative described by Formula VIII below:

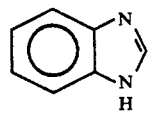

FORMULA VII

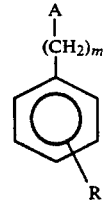

FORMULA VIII wherein m and R are as defined in Formula I, and A is a halogen atom.

The benzimidazole derivative of Formula IV is produced by N-alkylating the benzimidazole of Formula VII with the phenyl derivative of Formula VIII. This N-alkylation can be conducted utilizing techniques and reaction conductions known in the art.

Typically the benzimidazole derivative will be contacted with an alkali metal hydride, such as, for example, sodium hydride at room temperature. They will be stirred for a period of time ranging from about 10 minutes to about one hour. At that point, the phenyl derivative will be added and the reactants will be stirred for a period of time ranging from about 30 minutes to about 48 hours at room temperature. Typically a solvent such as dimethylformamide will be utilized. The benzimidazole derivative and the phenyl derivative will typically be present in approximately equimolar quantities, although a slight excess of either reactant is permissible. The alkali metal hydride is generally present in an approximately 10% molar excess.

The benzimidazole derivative of Formula IV can be recovered by methods analogous to those described for the piperidinyl derivative of Formula III in the previous N-alkylation reaction. The resulting concentrate can be purified by normal purification techniques such as distillation or recrystallization.

Those piperidinyl benzimidazole derivatives of Formula I in which Y is represented by CO and X is represented by either hydrogen or an alkylene phenyl derivative of Formula II in which T is a carbonyl group (CO), O or a direct bond can be produced in the following multi-step technique.

The first step is to alkylate the previously described benzimidazole derivative of Formula IV with a piperidinyl derivative as described by Formula IX below:

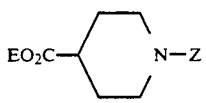

FORMULA IX wherein Z is an amino protecting group, such as a t-butoxy carbonyl group (t-Boc) and E is a $C_{1-4}$ alkyl.

This produces a piperidinyl benzimidazole intermediate as described by Formula X:

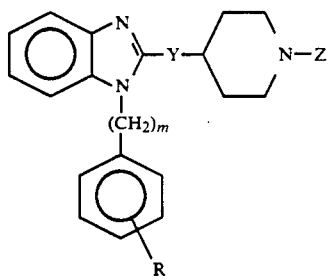

FORMULA X in which Y is represented by a carbonyl group, Z is a amino-protecting group, and m and R are as defined in Formula I.

This alkylation is conducted analogously to the alkylation reaction between the piperidinyl derivative of Formula III and the benzimidazole derivative of Formula IV described previously. The intermediate of Formula X can also be recovered and purified using techniques analogous to those used in the recovery and purification of the piperidinyl benzimidazole derivatives of Formula I which was described above.

The piperidinyl benzimidazole derivative of Formula I in which X is represented by hydrogen can then be produced by merely removing the amino protecting group, Z, from the piperidinyl benzimidazole intermediate of Formula X. This can be accomplished using techniques known in the art. For example if the amino protecting group is a t-Boc substituent, then it can be removed by hydrolysis with an acid such as trifluoroacetic acid.

Those piperidinyl benzimidazole derivatives of Formula I in which X is an alkylene phenyl derivative in which T is CO, O or a direct bond can be produced in the following manner. Initially, the amino protecting group, Z, is removed in the manner taught above. The deprotected intermediate of Formula X, in which Z is represented by hydrogen, is then N-alkylated with an alkylene phenyl derivative as previously described by Formula VI, except that T can represent CO, as well as O or a direct bond.

This N-alkylation is conducted in a manner analogous to the N-alkylation reaction between the piperidinyl derivative of Formula V and the alkylene phenyl derivative of Formula VI described above. The piperidinyl benzimidazole product can be recovered and purified using the same techniques described earlier for the recovery and purification of the compounds of Formula I.

As in the synthetic method discussed utilizing the compounds of Formula III and IV, it is preferred that the non-reacting substituents appearing in the starting materials be analogous to those appearing in the final product.

For example in order to produce [1-[(4-fluorophenyl)methyl]-1H-benzimidazol-2-yl][1-[2-(4-methoxyphenyl)ethyl]-4-piperidinyl]methanone using this method, one would react 1-[(4-fluorophenyl)methyl]-1H-benzimidazole with 1-(1,1-dimethylethyl)-1,4-piperidine dicarboxylic acid, 4methyl ester thereby producing the piperidinyl benzimidazole intermediate of Formula X, 4-[[1-[(4-fluorophenyl)methyl]-1H-benzimidazol-2-yl]carbonyl]-1-piperidinecarboxylic acid, 1,1-dimethylethyl ester. After removal of the amino protecting group, this intermediate is then reacted with 1-(2-bromoethyl)-4-methoxybenzene thereby producing [1-[(4-fluorophenyl)methyl]-1H-benzimidazol-2-yl][1-[2-(4-methoxyphenyl)ethyl]-4-piperidinyl]methanone.

Methods for producing the piperidinyl derivative of Formula IX are known in the art. An amino protecting group is added to the previously described piperidinyl derivative of Formula V. For example, if Z is a t-butoxy carbonyl substituent, (t-BOC) then it can be produced by contacting isonipecotic acid alkyl ester with di-ti-butyl dicarbonate in the presence of a base. Typically the base and the reactants are present in approximately equimolar quantities. The piperidinyl derivative of Formula IX can be recovered and purified by techniques known in the art such as extraction and distillation or recrystallization. Methods for producing the benzimidazole derivative of Formula IV have been discussed previously. The alkylene phenyl derivative of Formula VI as well as methods for its production are known in the art.

Those piperidinyl derivatives of Formula I wherein Y is represented by a hydroxymethylene group and X is represented by hydrogen, $COOR_2$, or an alkylene phenyl derivative in which T is O, or a direct bond can be produced in the following manner.

Initially a piperidinyl benzimidazole derivative as described by Formula I should be produced in which Y is represented by a carbonyl group and X is as defined above depending upon the desired compound This can be accomplished using the methods taught above.

This piperidinyl benzimidazole derivative is then subjected to a reduction reaction which converts the carbonyl group into a hydroxymethylene group. As is apparent to those skilled in the art, it is preferred that the non-reacting substituents appearing in this piperidinyl benzimidazole derivative correspond to those appearing in the desired final product.

For example, if the desired compound is 1-[(4-fluorophenyl)methyl]-α-[1-[2-(4-methoxyphenyl)ethyl]-4-piperidinyl-1H-benzimidazole-2-methanol then [1-1(4-fluorophenyl)methyl]-1H-benzimidazol-2-yl][1-[2-(4-methoxyphenyl)ethyl]-4-piperidinyl]-methanone is produced utilizing the methods described above. This compound is then reduced thereby producing the desired hydroxymethylene compound.

This reduction reaction can be accomplished utilizing techniques known in the art. Typically the carbonyl containing benzimidazole will be contacted with sodium or potassium borohydride in the presence of an alcohol. The reducing agent is generally present in the quantity of from about 1 to about 4 equivalents based on the quantity of piperidinyl benzimidazole present and more preferably from 1-2 equivalents. The reduction is conducted at a temperature ranging from room temperature to the reflux temperature of the solvent, more preferably room temperature.

This reduced piperidinyl benzimidazole can be recovered and purified using techniques analogous to those previously described for the compounds of Formula I.

Alternatively, the reduction can be conducted by hydrogenation utilizing catalysts such as platinum, ruthenium, etc; according to techniques known in the art.

Those piperidinyl benzimidazole derivatives of Formula I in which Y is a hydroxymethylene group and X is an alkylene phenyl group in which T is a carbonyl group, as well as O or a direct bond can be produced in the following manner.

Initially a piperidinyl benzimidazole derivative of Formula I should be produced in which Y is represented by a carbonyl group, X is represented by hydrogen and the non-reacting substituents are analogous to those appearing in the final product. This can be accomplished in the manner taught above.

This derivative is then subjected to a reduction reaction in the manner described above. After recovery and purification by the methods described above for the intermediate of Formula X, the reduced piperidinyl benzimidazole derivative is then subjected to an N-alkylation reaction with an alkylene phenyl derivative as defined by Formula VI in which T is represented by CO, O or a direct bond and the non-reacting substituents are analogous to those appearing in the final product. This N-alkylation can be accomplished in a manner analogous to the N-alkylation reaction between the piperidinyl derivative of Formula V and the alkylene phenyl derivative of Formula VI previously discussed.

The piperidinyl benzimidazole derivatives of Formula I in which X is an alkylene phenyl derivative and both Y and T are represented hydroxymethylene groups can be produced in the following manner. Initially a piperidinyl benzimidazole derivative of Formula I is produced wherein Y and T are both carbonyl groups, and the rest of the molecule is structurally analogous to the desired compound. This compound is then reduced in the manner taught above thereby producing the desired piperidinyl benzimidazole. The reduced piperidinyl benzimidazole product can then be recovered and purified by the methods taught above for the other compounds of Formula I.

The compounds of Formula I in which Y is a carbonyl group and X is an alkylene phenyl derivative in which T is a hydroxymethylene group can be formed in the following manner.

Initially an alkylene phenyl derivative as described by Formula VI should be formed in which T is represented by a hydroxymethylene group. The other non-reacting substituents appearing the molecule should be analogous to those appearing in the final product. This can be done utilizing techniques known in the art.

The next step in the reaction sequence is to place an appropriate protecting group on the hydroxyl group of the alkylene phenyl derivative. This can be accomplished by contacting the alkylene phenyl derivative with a moderate molar excess of a silylating agent such as hexamethyl disilazane, trimethylsilyl chloride, or bis-trimethylsilyl trifluoroacetamide. The reaction is conducted at room temperature utilizing techniques known in the art. This protected alkylene phenyl derivative can be recovered and purified by techniques known in the art.

An N-alkylation reaction is then conducted between the protected alkylene phenyl derivative and a piperidinyl benzimidazole derivative of Formula I wherein Y is a carbonyl group, X is hydrogen and the non-reacting substituents appearing in the piperidinyl benzimidazole derivative are analogous to those appearing in the final product. This N-alkylation can be accomplished in a manner analogous to the N-alkylation reaction between the piperidinyl derivative of Formula V and the alkylene phenyl derivative of Formula VI previously discussed.

The desired compound of Formula I can then be produced by removing the silane protecting group from the indicated hydroxyl function. This can be accomplished using techniques known in the art such as contacting the protected piperidinyl benzimidazole derivative with a source of fluoride ions.

Typically the protected piperidinyl benzimidazole derivative will be contacted with an organic source of fluoride ions such as tetrabutyl ammonium fluoride ($Bu_4N^+F^-$) in the presence of organic solvent such as methanol, for a period of time ranging from 0.5 hours to 6 hours at room temperature. The desired piperidinyl benzimidazole derivative can be recovered by extraction, after water has been added to the reaction zone and purified by recrystallization from a solvent system such as cyclohexane.

In order to produce those compounds of Formula I in which $R_1$ is represented by 2,2-dimethyl ethanoic acid, the following synthetic method should be followed.

Initially a piperidinyl benzimidazole as described by Formula I should be prepared in which X is represented by hydrogen, Y is either CO or CHOH depending upon the desired product, and the other non-reacting substituents are analogous to those appearing in the final product.

This piperidinyl benzimidazole is then N-alkylated with an alkylene phenyl derivative as described by Formula XI below:

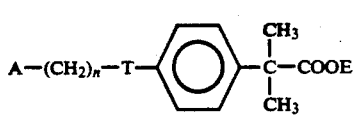

FORMULA XI wherein A is represented by a halogen atom, E is represented by a $C_{1-4}$ alkyl, T is either as defined in Formula I or is a silane protected hydroxymethylene group, n is as in Formula I, and the non-reacting substituents are analogous to those appearing in the final product This N-alkylation reaction can be conducted in a manner analogous to that previously described for the piperidinyl derivative of Formula V and the alkylene phenyl derivative of Formula VI.

This N-alkylation reaction produces the following product:

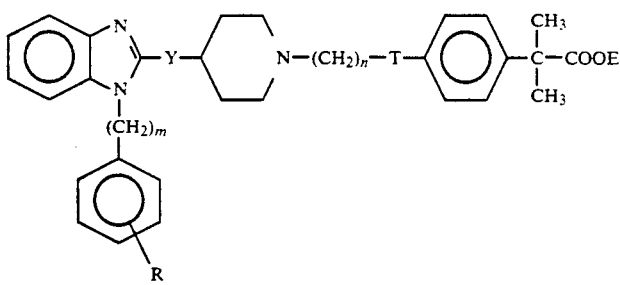

FORMULA XII wherein Y, n, m, and R are as defined in Formula I and E and T are as defined above The compounds encompassed by this formula can then be subjected to the various reduction and deprotection reactions outlined above, as is required to produce a product in which Y and T are the proper substituents. This can be done by the methods outlined above. These various reactions should be completed prior to the final step of the synthesis which is the hydrolysis of the alkyl ester represented by $CO_2E$.

Once a compound is obtained in which Y and T are the desired groups, the desired product can then be obtained by subjecting this compound to an alkaline hydrolysis reaction which serves to hydrolyse the ester group to the corresponding carboxylic acid. This hydrolysis can be conducted using techniques which are known in the art. Typically the compound is contacted with large molar excess of a base such as sodium hydroxide in the presence of aqueous alcoholic solvent at a temperature range of from about 20° C. to about 100° C.

Following neutralization, the desired product can be recovered and purified by the methods taught above for the compounds of Formula I.

The compounds of Formula I wherein Y is represented by CO and X is an alkylene phenyl derivative in which T is represented by CO can also be made via the following alternative synthesis. Initially an alkylation reaction is conducted between an N-protected benzimidazole as described by Formula XIII and a piperidinyl derivative as described by Formula XIV:

In the protected benzimidazole of Formula XIII, P is represented by a silane protecting group such as —$CH_2$-O-$(CH_2)_2$-Si-$(CH_3)_3$ (SEM group). In the piperidinyl derivative of Formula XIV, E is represented by a $C_{1-4}$ alkyl, B is

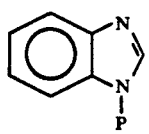

FORMULA XIII

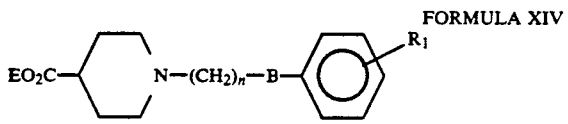

FORMULA XIV represented by a ketal protecting group, and both n and $R_1$ are as defined in Formula I.

This acylation reaction produces an intermediate as described by Formula XV below:

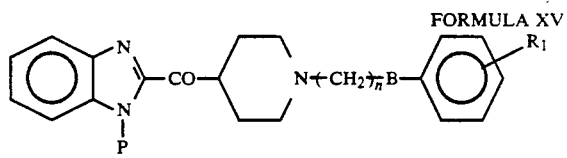

FORMULA XV wherein P, n, B and $R_1$ are as defined immediately above.

The acylation between the protected benzimidazole of Formula XIII and the piperidinyl derivative of Formula XIV can be conducted in a manner analogous to the reaction between the piperidinyl derivative of Formula II and the benzimidazole derivative of Formula IV described above. The product of Formula XV can be recovered by the addition of water to the reaction zone and extraction with an organic solvent. The product can be optionally purified by techniques such chromatographic separation or recrystallization from an appropriate solvent system. Other techniques known in the art may also be utilized.

The next step in the reaction is to submit the benzimidazole of Formula XV to a hydrolysis reaction, thus producing a compound wherein P is represented by H and B is represented by CO. This can be accomplished by contacting the intermediate of Formula XV with an acid such as hydrochloric acid, at a temperature range of 0° C. to 100° C. for a period of time ranging from 0.5 hours to 6 hours.

The desired compound of Formula I can then be formed by N-alkylating the deprotected intermediate of Formula XV, in which P is represented by a hydrogen atom, with a phenyl derivative as described by Formula VIII below:

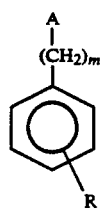

FORMULA VIII in which A is represented by a halogen atom and both m and R are as defined in Formula I.

This N-alkylation can be conducted in a manner analogous to the N-alkylation described previously between the benzimidazole of Formula VII and the phenyl derivative of Formula VIII. The desired compound of Formula I can then be recovered and purified utilizing the methods described above in the other synthetic procedures for recovering and purifying the compounds of Formula I.

The protected benzimidazole starting material of Formula XIII can be produced utilizing techniques known in the art. Typically the benzimidazole of Formula VII will be contacted with a 10% molar excess of NaH and then with a molar excess of a silane protecting agent such as Cl-CH$_2$-O-(CH$_2$)$_2$-Si-(CH$_3$)$_3$ for a period of time ranging from 30 minutes to 1 hour. The reaction is typically conducted in an aprotic solvent such as dimethylformamide at a temperature range of from 0° C. to 50° C. The protected benzimidazole of Formula XIII can be recovered and purified using techniques known in the art, such as, for example kugelrohr distillation.

Methods for producing the piperidinyl starting material of Formula XIV are also known in the art. The piperidinyl derivative of Formula XIV is produced by contacting a piperidinyl derivative as described by Formula XVII below,

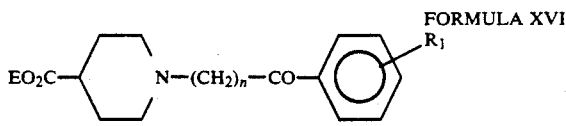

FORMULA XVI in which E is represented by a C$_{1-4}$ alkyl and R$_1$ is as defined in Formula I; with a large molar excess of a diol, such as ethylene glycol, in the presence of an acid catalyst such as p-toluenesulfonic acid. The reaction is typically conducted at a temperature range of from 50° C. to 120° C. for a period of time ranging from 1 to 48 hours in an organic solvent such as toluene or benzene. The piperidinyl derivative of Formula XIV can be recovered and purified using techniques know in the art.

As noted above, the compounds are antihistamines and thus are useful in the treatment of allergic diseases. Some are also peripheral serotonin 5HT$_2$ antagonists.

One method of demonstrating the compounds utility as antihistamines is the following test protocol. One group of 10 guinea pigs is dosed orally with from about 0.1 mg/kg to about 100 mg/kg of the test compound. A control group of 10 guinea pigs is dosed orally with a similar volume of vehicle (a solution of 0.5% methylcellulose and 1% ethanol). Both groups should be anesthetized and their dorsal areas shaved. One hour later, both groups are given intravenous injections of 1% Evans Blue Dye (1 ml) via the jugular vein. Immediately following the dye injection, both groups are injected intradermally in the dorsal area with histamine diphosphate injections (1 µg/0.1 ml) to produce histamine wheals. Twenty minutes after injection of the histamine, the animals are sacrificed and the size of the wheal area is then calculated from the diameter of the exposed wheal. A compound is considered to possess antihistamine activity if the wheal area of the drug treated group is statistically smaller than that of the control group.

The compounds are useful in the treatment of a variety allergic diseases. Examples of allergic diseases amenable to treatment with the compounds of Formula I include allergic rhinitis, seasonal rhinitis, allergic dermatoses such as acute urticaria, atopic dermatitis, and contact dermatitis. Other examples include gastrointestinal allergies which can be caused by the ingestion of either food or drugs. The compounds can also be used in the treatment of allergic pulmonary disease such as, for example, allergic asthma. Opthalmic allergies also respond to the compounds of Formula I.

The dosage range (an antihistaminic amount) at which these compounds exhibit their antihistaminic effect can vary widely depending upon the particular allergic disease being treated, the severity of the patient's disease, the patient, the particular compound being administered, the route of administration, and the presence of other underlying disease states within the patient, etc. Typically the compounds exhibit their antihistaminic effect at a dosage range of from about 0.01 mg/kg/day to about 120 mg/kg/day. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, or introperitoneally). The compounds can be introduced directly into the respiratory tract by methods such as inhalation therapy, nasal sprays, nasal drops, etc. Topical preparations of the compounds can be applied directly to the skin.

Pharmaceutical compositions can be manufactured utilizing techniques known in the art. Typically an antihistaminic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin The pharmaceutical carrier may also contain preservatives, buffers, etc., as are known in the art.

For nasal administration, the compounds may be dissolved in a physiologically acceptable pharmaceutical carrier and administered as a solution Illustrative of suitable pharmaceutical carriers are water, saline, and aqueous alcoholic solutions. The pharmaceutical carrier may also contain preservatives, buffers, etc., as are known in the art.

For topical administration, the compounds can incorporated into a suitable topical carrier using techniques well known in the art. Examples of suitable topical carriers include oleaginous bases such as white petrolatum, absorption bases such as hydrophilic petrolatum, emulsion bases such as lanolin, and water soluble bases such as polyethylene glycol ointment. The topical carrier may also contain preservatives, buffers, etc., as are known in the art.

For inhalation therapy, the compounds can be incorporated into an aqueous alcoholic solution containing a fluorinated hydrocarbon propellant and packaged into a suitable administration device as known in the art.

As used in this application:
a) the term patient refers to warm blooded animals such as, for example, guinea pigs, mice, rats, cats, rabbits, dogs, monkeys, chimpanzees, and humans;
b) the term allergic disease refers to a condition in which the effect of histamine on the $H_1$ receptor has an adverse effect upon the patient, and,
c) the term treat refers to the ability of the compound to either relieve or alleviate the patient's disease.

The following examples are presented in order to further illustrate the invention. They should not be construed as limiting the invention in any manner.

EXAMPLE I

The purpose of this example is to demonstrate one method for the preparation of a benzimidazole derivative of Formula IV.

To a stirred, room temperature, solution of benzimidazole (11.8 g, $1.00 \times 10^{-1}$ mole) and dry DMF (100 ml) was added portion-wise sodium hydride (4.4 g, $1.1 \times 10^{-1}$ mole, 60% oil dispersion). After ca. 30 minutes, 4-fluorobenzyl chloride (14.6 g, $1.01 \times 10^{-1}$ mole) was added. The reaction was stirred at room temperature for ca. 17 hours and was then poured into a separatory funnel containing water and a 2:1 mixture of ethyl acetate:toluene. The two phases were mixed and the aqueous layer was separated. The organic layer was washed two times with H20 and once with saturated aqueous NaCl before being dried over anhydrous Na$_2$SO$_4$. The drying agent was removed by filtration and the filtrate was evaporated at reduced pressure leaving an oil which was purified by flash chromatography (20% acetone/ethyl acetate). The resulting oil was kugelrohr distilled (230–245° C./0.3 mm) affording 1-[(4-fluorophenyl)methyl]-1H-benzimidazole as an oil which solidified giving a colorless solid: 17.4 g (77%), m.p. 60–62° C.

Analysis Calculated for $C_{14}H_{11}FN_2$: C, 74.32; H, 4.90; N, 12.38. Found: C, 74.25; H, 4.94; N, 12.23.

EXAMPLE II

The purpose of this example is to demonstrate one method for the preparation of a piperidinyl intermediate of Formula III.

To a stirred, room temperature, mixture of isonipecotic acid methyl ester hydrochloride (5.00 g, $2.78 \times 10^{-2}$ mole), potassium carbonate (7.70 g, $5.57 \times 10^{-2}$ mole), and DMF (100 ml) was added 1-(2-bromoethyl)-4-methoxybenzene (5.99 g, $2.78 \times 10^{-2}$ mole). The reaction was then immersed in an oil bath which had been preheated to ca. 90° C. The reaction was heated at ca. 90° C. for ca. 17 hours and was then poured into a separatory funnel containing water and a 2:1 mixture of ethyl acetate:toluene. The two phases were mixed and the aqueous layer was separated. The organic layer was washed two times with H$_2$O and once with saturated aqueous NaCl before being dried over anhydrous Na$_2$SO$_4$. The drying agent was removed by filtration and the filtrate was evaporated at reduced pressure leaving an oil. Purification by flash chromatography (ethyl acetate) and crystallization from cyclohexane gave 1-[2-(4-methoxyphenyl)ethyl]-4-piperidinecarboxylic acid, methyl ester as a colorless solid: 3.98 g (52%), m.p. 66–68° C.

Analysis Calculated for $C_{16}H_{23}NO_3$: C, 69.29; H, 8.36, N, 5.05. Found: C, 69.50; H, 8.40; N, 4.94.

EXAMPLE III

The purpose of this example is to demonstrate one method for the preparation of the piperidinyl benzimidazole derivatives of Formula I.

To a stirred, −78° C., solution of 1-[(4-fluorophenyl)methyl]-1H-benzimidazole (1.13 g, $5.00 \times 10^{-3}$ mole) and dry THF (12 ml) under argon was added a 2.5 molar hexane solution of n-butyl lithium (2.1 ml, $5.25 \times 10^{-3}$ mole). After 15–20 minutes at −78° C., a solution of 1-[2-(4-methoxyphenyl)ethyl]-4-piperidinecarboxylic acid, methyl ester (1.39 g, $5.01 \times 10^{-3}$ mole) and dry THF (6 ml) was added dropwise via syringe. After 5–10 minutes, the cooling bath was removed and the reaction was allowed to warm. After ca. 30 minutes, the reaction was quenched by the addition of saturated aqueous NH$_4$Cl. The reaction was transferred to a separatory funnel where the aqueous mixture was extracted two times with ethyl acetate. The ethyl acetate extracts were combined, washed with saturated aqueous NaCl, and dried over anhydrous Na$_2$SO$_4$. The drying agent was removed by filtration and the filtrate was evaporated at reduced pressure affording a viscous oil. This was purified by a combination of flash chromatography (ethyl acetate) and crystallization (cyclohexane) affording 1-[(4-fluorophenyl)methyl]-1H-benzimidazol-2-yl][1-[2-(4methoxyphenyl)ethyl]-4-piperidinyl]methanone as off white matted needles: 0.90 g (38%), m.p. 109–111° C.

Analysis Calculated for $C_{29}H_{30}FN_3O_2$: C, 73.86; H, 6.41, N, 8.91. Found: C, 73.98; H, 6.48; N, 8.90.

EXAMPLE IV

The purpose of this example is to demonstrate one method for the preparation of a piperidinyl intermediate as described by Formula IX.

To a stirred suspension of isonipecotic acid, methyl ester hydrochloride (5.00 g, $2.78 \times 10^{-2}$ mole) and t-butanol (56 ml) was added a 1 molar aqueous solution of NaOH (29 ml, $2.9 \times 10^{-2}$ mole). After all the starting ester had dissolved, di-t-butyl dicarbonate (6.68 g, $3.06 \times 10^{-2}$ mole) was added. After being stirred two days, the excess t-butanol was evaporated at reduced pressure. The concentrate was diluted with H$_2$O, transferred to a separatory funnel, and extracted three times with ethyl acetate. The ethyl acetate extracts were combined, washed with saturated aqueous NaCl, and dried over anhydrous Na$_2$SO$_4$. The drying agent was removed by filtration and the filtrate was evaporated at reduced pressure leaving an oil. Kugelrohr distillation gave 1-(1,1-dimethylethyl)-1,4-piperidinedicarboxylic acid, 4-methyl ester as a clear, colorless liquid: 6.21 g (92%), b.p. 160–170. (0.2–0.3 mm).

Analysis Calculated for $C_{12}H_{21}NO_4$: C, 59,24; H, 8.70; N, 5.76. Found: C, 58.92; H, 8.76; N, 5.45.

EXAMPLE V

The purpose of this example is to demonstrate one method for the preparation of a piperidinyl benzimidazole intermediate of Formula X.

To a stirred, −78° C., solution of 1-[(4-fluorophenyl)methyl]-1H-benzimidazole (9.80 g, $4.62 \times 10^{-2}$ mole) and dry THF (80 ml), under argon, was added dropwise via syringe a 2.5 molar solution of n-butyl lithium in hexane (20.0 ml, 5.00×10$^{-2}$ mole). After ca. 5 minutes at −78° C., a 0° C. solution of 1-(1,1-dimethylethyl)-1,4-piperidinedicarboxylic acid, 4-methyl ester (11.24 g, 4.62×10$^{-2}$ mole) and dry THF (30 ml) was added dropwise via syringe. After 15 minutes, the reaction was quenched by the addition of methanol (10 ml). After an additional 5 minutes the reaction was poured into a separatory funnel containing saturated aqueous NH$_4$Cl. The aqueous layer was extracted three times with ether. The separated organic extracts were combined, washed with saturated aqueous NaCl, and dried over anhydrous Na$_2$SO$_4$. The drying agent was removed by filtration and the filtrate was evaporated at reduced pressure leaving a pale yellowish foam. This was purified by flash chromatography (20% ethylacetate/hexane) and crystallization (cyclohexane) affording 4-[1-[(4-fluorophenyl)methyl]-1H-benzimidazol-2-yl]carbonyl-1-piperidinecarboxylic acid, 1,1-dimethylethyl ester as a colorless solid: 6.8 g (34%), m.p. 114–115° C.

Analysis calculated for C$_{25}$H$_{28}$FN$_3$O$_3$: C, 68.63; H, 6.45; N, 9.60. Found C, 68.81; H, 6.51, N, 9.56.

EXAMPLE VI

The purpose of this example is to demonstrate one method for removing the amino protecting group from the piperidinyl benzimidazole intermediate of Formula X as produced in Example V.

With stirring, trifluoroacetic acid (10 ml) was added to 4-[1-[(4-fluorophenyl)methyl]-1H-benzimidazol-2-yl]carbonyl-1-piperidinecarboxylic acid, 1,1-dimethylethyl ester (1.65 g, 3.77×10$^{-3}$ mole). After 30 minutes the reaction was cooled in an ice bath and ether (150 ml) was added. The flask was stoppered and placed in the refrigerator. After several hours, the solid was collected by filtration, washed with Et$_2$O, and dried by suction. Crystallization from ethanol/ether afforded [1-[(4-fluorophenyl)methyl]-1H-benzimidazol-2-yl]-4-piperidinylmethanone, mono (trifluoroacetate) as colorless needles: 1.45 g (84%), m.p. 213–215° C. (decomp).

Analysis calculated for C$_{20}$H$_{20}$FN$_3$O.CF$_3$CO$_2$H: C, 58.54; H, 4.69; N, 9.31. Found: C, 58.55; H, 4.77; N, 9.29.

EXAMPLE VII

The purpose of this example is to demonstrate another method for the preparation of a piperidinyl benzimidazole derivative of Formula I.

To a stirred, room temperature, mixture of [1-[(4-fluorophenyl)methyl]-1H-benzimidazol-2-yl]-4-piperidinylmethanone, mono (trifluoroacetate) (1.82 g, 4.03×10$^{-3}$ mole), potassium carbonate (1.39 g, 1.00×10$^{-2}$ mole), and sieve dry DMF (15 ml) was added 1-(2-bromoethyl)-4-methoxybenzene (0.87 g, 4.04×10$^{-3}$ mole). The reaction was then immersed in an oil bath which had been preheated to ca. 90° C. After being stirred at between 80–90° C. for 22 hours, the reaction was allowed to cool to room temperature. The reaction was poured into a separatory funnel containing H$_2$O and a 2:1 mixture of ethyl acetate:toluene. The two phases were mixed and the aqueous layer was separated. The organic layer was washed two times with H$_2$O and once with saturated aqueous NaCl before being dried over anhydrous Na$_2$SO$_4$. The drying agent was removed by filtration and the filtrate was evaporated at reduced pressure leaving an oil which was purified by flash chromatography (ethyl acetate). Crystallization from cyclohexane afforded [1-[(4-fluorophenyl)methyl]-1H-benzimidazol-2-yl][1-[2-(4-methoxyphenyl)ethyl]-4-piperidinyl]methanone as off white matted needles: 1.08 g (57%). This material was spectroscopically identical with the previously described product of Example III.

This product exists as polymorphs the melting point of one being 109–111° C. and the melting point of the other being 125–126° C.

EXAMPLE VIII

The purpose of this example is to demonstrate the preparation of another piperidinyl benzimidazole of Formula I.

[1-[(4-fluorophenyl)methyl]-1H-benzimidazol-2-yl]-4-piperidinylmethanone mono (trifluoroacetate) (5.0 g, 11 mmol), 4-chloro-4'-tert-butylbutyrophenone (6.2, 26 mmol), potassium bicarbonate (2.5 g, 25 mmol), and potassium iodide (catalytic amount) were combined and refluxed in toluene (50 ml) and water (5 ml) for 3 days. The cooled layers were separated and the aqueous layer was extracted with ethyl acetate. The combined organic layers were washed with water, brine, dried (MgSO$_4$), and concentrated. The resulting oil was chromatographed on silica gel (75×160 mm), eluting with ethyl acetate. The appropriate fractions were combined, concentrated, and the resulting oil crystallized from cyclohexane to afford 1-[4-(1,1-dimethylethyl)phenyl]-4-[4-[[1-[(4-fluorophenyl)methyl]-1H-benzimidazol -2-yl]carbonyl]-1-piperidinyl]-1-butanone: 3.4 g (57%), m.p. 105–106° C.

Anal. Calcd. for C$_{34}$H$_{38}$FN$_3$O$_2$: C, 75.67; H, 7.10; N, 7.79. Found: C, 75.65; H, 7.16; N, 7.78.

EXAMPLE IX

The purpose of this example is to demonstrate the preparation of a piperidinyl benzimidazole of Formula I in which Y is represented by CHOH.

To a stirred, 0° C., solution of [1-[(4-fluorophenyl)methyl]-1H-benzimidazol-2-yl][1-[2-(4-methoxyphenyl)ethyl]-4piperidinyl]methanone (1.28 g, 2.71×10$^{-3}$ mole) and methanol (20 ml), was added NaBH$_4$ (0.10 g, 2.6×10$^{-3}$ mole). After 2 hours another equivalent of NaBH$_4$ (0.10 g, 2.6×10$^{-3}$ mole) was added. After an additional 2 hours, the methanol was evaporated at reduced pressure. The concentrate was dissolved in a two phase mixture of EtOAc and H$_2$O. The layers were separated and the aqueous layer was re-extracted two times with EtOAc. The EtOAc layers were combined, washed with saturated aqueous NaCl, and dried over anhydrous Na$_2$SO$_4$. The drying agent was removed by filtration and the filtrate was evaporated at reduced pressure leaving a foam. Flash chromatography (25% CH$_3$OH/EtOAc) afforded 1-[(4-fluorophenyl)methyl]-α-[1-[2-(4-methoxyphenyl)ethyl]-4-piperidinyl]-1H-benzimidazole-2-methanol.

EXAMPLE X

The purpose of this example is to demonstrate the preparation of a piperidinyl benzimidazole of Formula I in which both Y and T are represented by —CHOH.

To a stirred, room temperature, solution of 1-[4-(1,1-dimethylethyl)phenyl]-4-[4-[[1-[(4-fluorophenyl)methyl]-1H-benzimidazol-2-yl]carbonyl]-1-piperidinyl]-1-butanone (2.1 g, 3.9×10$^{-3}$ mole) and methanol (80 ml) was added NaBH$_4$ (0.42 g, 1.1×10$^{-2}$ mole). After stirring overnight, the methanol was evaporated at reduced pressure. The concentrate was dissolved in a two phase mixture of EtOAc/H$_2$O. The layers were separated and the aqueous layer was re-extracted with EtOAc. The EtOAc extracts were combined, washed with saturated aqueous NaCl, and dried over anhydrous MgSO$_4$. The drying agent was removed by filtration and the filtrate was evaporated at reduced pressure leaving a solid. Crystallization from cyclohexane/hexane afforded α-[1-[4-[4-(1,1-dimethylethyl)phenyl]-4-hydroxybutyl]-4-piperidinyl]-1-[(4-fluorophenyl)methyl]-1H-benzimidazole-2-methanol as a colorless solid: 1.6 g (75%), m.p. 87–90° C.

What is claimed is:

1. A process for producing a piperidinyl benzimidazole of the formula:

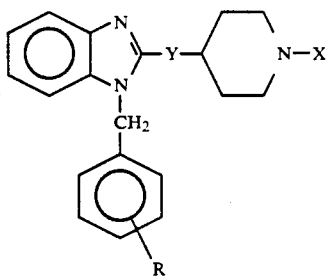

wherein Y is represented by CO; R is represented by $C_{1-4}$ alkyl, $C_{1-4}$ alkoxy, halogen, hydroxy and hydrogen, X is COOR$_2$ in which R$_2$ is represented by a $C_{1-4}$ alkyl, or X is an alkylene phenyl radical of the formula:

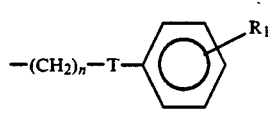

wherein T is represented by O, or a direct bond; R$_1$ is represented by $C_{1-4}$ alkyl, $C_{1-4}$ alkoxy, halogen, hydroxy, 2,2-dimethyl ethanoic acid and hydrogen; n is an integer from 1 to 5; or a pharmaceutically acceptable acid addition salt thereof; comprising: carrying out an acylation reaction between:

a) a benzimidazole of the formula

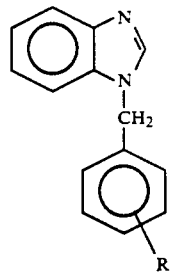

wherein R is as defined above, and;
b) a piperidinyl derivative of the formula:

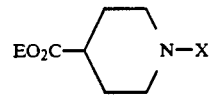

wherein X is as defined above and E is a $C_{1-4}$ alkyl;
c) in the presence of n-butyl lithium.

2. A process according to claim 1 wherein said acylation reaction is carried out by contacting the benzimidazole with the n-butyl lithium and subsequently adding the piperidinyl derivative to the reaction.

3. A process according to claim 2 wherein said benzimidazole and said n-butyl lithium are contacted to a temperature range of from −50° to −90° C. for a period of time from about 5 to about 30 minutes.

4. A process according to claim 3 wherein the reaction is warmed to about 0° C. after the piperidinyl derivative is added to the reaction.

5. A process according to claim 4 wherein X is represented by COOR$_2$.

6. A process according to claim 4 wherein X is t-butoxy carbonyl.

7. A process according to claim 4 wherein X is represented by said alkylene phenyl derivative.

* * * * *